(12) United States Patent
Kato et al.

(10) Patent No.: US 7,872,480 B2
(45) Date of Patent: Jan. 18, 2011

(54) GAS SENSOR CONTROL APPARATUS

(75) Inventors: Kenji Kato, Aichi (JP); Hisashi Sasaki, Aichi (JP); Koji Shiotani, Aichi (JP)

(73) Assignee: NGK Spark Plug Co., Ltd., Nagoya, Aichi (JP)

( * ) Notice: Subject to any disclaimer, the term of this patent is extended or adjusted under 35 U.S.C. 154(b) by 196 days.

(21) Appl. No.: 12/197,495

(22) Filed: Aug. 25, 2008

(65) Prior Publication Data
US 2009/0051373 A1    Feb. 26, 2009

(30) Foreign Application Priority Data

Aug. 23, 2007  (JP) .............................. 2007-217677
Apr. 8, 2008   (JP) .............................. 2008-100407

(51) Int. Cl.
*G01N 27/04* (2006.01)

(52) U.S. Cl. ................. 324/691; 324/693; 204/406; 204/424; 205/775

(58) Field of Classification Search ........... 324/693, 324/691; 374/141; 204/406, 424; 205/775
See application file for complete search history.

(56) References Cited

U.S. PATENT DOCUMENTS 6,228,252 B1     5/2001  Miyata et al.
2004/0047396 A1*  3/2004  Nomura et al. ............. 374/141

* cited by examiner

*Primary Examiner*—Vincent Q Nguyen
(74) *Attorney, Agent, or Firm*—Stites & Harbison PLLC; Jeffrey A. Haeberlin

(57) ABSTRACT

A gas sensor control apparatus for controlling a gas sensor includes a resistance detection unit and a heater control unit. The resistance detection unit detects a resistance of an object cell of the gas sensor. When the resistance of the object cell is lower than a predetermined threshold, the heater control unit controls energization of a heater such that the resistance detected by the resistance detection unit is a first predetermined resistance. Subsequently, after elapse of a predetermined time, the heater control unit further controls energization of the heater in such a manner that the resistance detected by the resistance detection unit is a second predetermined resistance of a resistance value that is higher than that of the first predetermined resistance.

20 Claims, 8 Drawing Sheets

GAS SENSOR CONTROL APPARATUS

BACKGROUND OF THE INVENTION

1. Field of the Invention

The present invention relates to a gas sensor control apparatus for controlling a gas sensor including a gas sensor element adapted to detect the concentration of $NO_x$ gas, ammonia gas, or a like gas, and more particularly, to a gas sensor control apparatus which performs heater control processing for activating the gas sensor element through application of heat by a heater.

2. Description of Related Art

A conventionally known gas sensor element has a first measurement chamber, a first oxygen pump cell, a second measurement chamber, a second oxygen pump cell, a reference-oxygen chamber, and an oxygen-concentration detection cell (refer to, for example, Japanese Patent Application Laid-Open (Kokai) No. 10-288595). In the gas sensor element, each of the first oxygen pump cell and the oxygen-concentration detection cell is configured such that an oxygen-ion-conductive solid electrolyte layer has porous electrodes provided on respective opposite sides of the cell. Also, the first measurement chamber communicates with an object gas (an "object gas of measurement") atmosphere via a first diffusion control layer, and the second oxygen pump cell is configured such that an oxygen-ion-conductive solid electrolyte layer has porous electrodes provided on respective opposite sides of the layer. By use of a sensor body which has the above-mentioned cells and in which the second measurement chamber communicates with the first measurement chamber via a second diffusion control layer, the $NO_x$ concentration of an object gas is detected.

Specifically, a pump-current control means causes the first oxygen pump cell to pump oxygen out from the first measurement chamber such that an output voltage of the oxygen-concentration detection cell becomes constant, thereby controlling the object gas flowing into the second measurement chamber from the first measurement chamber to have a constant oxygen concentration. A constant-voltage application means applies a constant voltage to the second oxygen pump cell in such a direction as to pump out oxygen from the second measurement chamber. On the basis of current which flows through the second oxygen pump cell as a result of application of the constant voltage, a nitrogen-oxide-concentration detection means detects the $NO_x$ concentration of the object gas.

In order to accurately detect the $NO_x$ concentration by the above-mentioned method, the conventional nitrogen-oxide-concentration detection apparatus has a heater for heating the cells, since the gas sensor element must be heated to a predetermined activation temperature (e.g., 800° C. or higher) for activating the cells. The temperature of the gas sensor element is controlled as follows. The internal resistance of the oxygen-concentration detection cell is detected. With reference to a sensor temperature obtained on the basis of the detected internal resistance, energization of the heater is controlled. In another conventional gas sensor element, after the heater is energized, energization of the heater is controlled in such a manner that the oxygen-concentration detection cell assumes a target internal resistance.

However, the above-mentioned conventional gas sensor element tends to consume much time (herein, the time is called the activation time) until a sensor output (current flowing between the electrodes of the second oxygen pump cell) used to detect concentration of a specific gas (concentration of $NO_x$ gas) stabilizes to a value corresponding to a target concentration range (a "target concentration range of measurement"). Thus, a relatively long waiting time after startup of the gas sensor element must be set before the stabilization.

BRIEF SUMMARY OF THE INVENTION

The present invention addresses the above-mentioned problem and others. One object of the invention is to provide a gas sensor control apparatus which can shorten activation time, as compared with the conventional activation time, for a gas sensor element having a plurality of cells and a heater for heating the plurality of the cells, and configured such that current corresponding to a specific gas concentration of an object gas flows between electrodes of one of the plurality of cells.

According to a first aspect of the invention, a gas sensor control apparatus of an invention for controlling a gas sensor including a gas sensor element which has a plurality of cells. Each cell of the plurality of cells includes an oxygen-ion conductive member and a pair of electrodes formed on the oxygen-ion conductive member. The gas sensor also includes a heater for heating the plurality of cells. A current corresponding to a specific gas concentration of an object gas flows between the electrodes of one cell of the plurality of the cells. The gas sensor control apparatus comprises a resistance detection means for detecting a resistance of an object cell (an "object cell of measurement") comprising any one of the plurality of cells, and a heater control means for controlling energization of the heater in such a manner that the resistance detected by the resistance detection means is a first predetermined resistance, and subsequently further controlling energization of the heater in such a manner that the resistance detected by the resistance detection means is a second predetermined resistance of a resistance value that is greater than that of the first predetermined resistance.

According to a second aspect of the invention, a gas sensor control apparatus of an invention for controlling a gas sensor including a gas sensor element which has a plurality of cells. Each cell of the plurality of cells includes an oxygen-ion conductive member and a pair of electrodes formed on the oxygen-ion conductive member. The gas sensor also includes a heater for heating the plurality of cells. A current corresponding to a specific gas concentration of an object gas flows between the electrodes of one cell of the plurality of the cells. The gas sensor control apparatus comprises: a resistance detection means for detecting a resistance of an object cell comprising any one of the plurality of the cells; a first resistance determining means for determining whether the resistance detected by the resistance detection means is lower than a predetermined reference resistance; a cell energization start means for starting to energize the plurality of cells when the first resistance determining means determines that the resistance detected by the resistance detection means is lower than the predetermined reference resistance; and a heater control means for, when the first resistance determining means determines that the resistance detected by the resistance detection means is lower than the predetermined reference resistance, controlling energization of the heater in such a manner that the resistance detected by the resistance detection means is a first predetermined resistance of a resistance value that is lower than that of the predetermined reference resistance, and subsequently further controlling energization of the heater in such a manner that the resistance detected by the resistance detection means is a second predetermined resistance of a resistance value that is higher than that of the first predetermined resistance and lower than that of the reference resistance.

Advantageously, both the first and second aspects of the invention can shorten the time (activation time) that elapses after startup of the gas sensor element until the specific gas concentration of an object gas can be accurately determined from a target concentration range. Also, after energization of the heater is controlled so as to attain the first predetermined resistance, energization of the heater is controlled so as to attain the second predetermined resistance. This can restrain excessive heating of the gas sensor element. Thus, while deterioration of the gas sensor element is restrained, the activation time of the gas sensor element can be shortened as compared with conventional practice.

Further, the gas sensor control apparatus of the second aspect has the cell energization start means for starting to energize the plurality of cells when the first resistance determining means determines that the resistance detected by the resistance detection means is lower than the predetermined reference resistance. Thus, energization is started from a state where the internal resistances of the cells are relatively low, thereby restraining occurrence of an overvoltage between the electrodes of each of the cells. Also, from this point of view, deterioration of the gas sensor element can be restrained.

In one implementation, the gas sensor element includes, as the plurality of the cells: an oxygen-concentration detection cell for detecting an oxygen concentration of the object gas introduced into a first measurement chamber; a first oxygen pump cell for pumping out oxygen from or pumping oxygen into the object gas contained in the first measurement chamber based on the oxygen concentration detected by the oxygen-concentration detection cell, so as to generate an adjusted gas having a controlled oxygen concentration; and a second oxygen pump cell configured such that one electrode of the pair of electrodes of the second oxygen pump cell is disposed in a second measurement chamber which communicates with the first measurement chamber and into which the adjusted gas is introduced and such that the current corresponding to the specific gas concentration of the object gas flows between the pair of electrodes of the second oxygen pump cell through application of a predetermined voltage between the pair electrodes of the second oxygen pump cell. Advantageously, this implementation allows a shortening of the time (activation time) that elapses after startup of the gas sensor element until the specific gas concentration of an object gas can be accurately determined from the target concentration range.

In another implementation, the gas sensor control apparatus further comprises a voltage detection means for detecting a voltage of the object cell. When a voltage between the pair of electrodes of the object cell becomes lower than a predetermined threshold voltage, the resistance detection means starts to measure the resistance of the object cell. After startup of the gas sensor element, the drop in voltage between the pair of electrodes of the object cell means that the internal resistance of the object cell has dropped to a certain level. Therefore, by means of starting to measure the resistance of the object cell after the voltage between the paired electrodes of the object cell becomes lower than the predetermined threshold voltage, the internal resistance of the object cell can be stably detected without application of overvoltage between the paired electrodes of the object cell.

In yet another implementation, the object cell is the oxygen-concentration detection cell. Therefore, the temperature of the heater can be controlled on the basis of the resistance of the oxygen-concentration detection cell.

In still further another implementation, the gas sensor control apparatus satisfies a relation R2−R1≧50 ohms, where R1 is the first predetermined resistance, and R2 is the second predetermined resistance. This can more reliably shorten the time (activation time) that elapses after startup of the gas sensor element until the specific gas concentration of an object gas can be accurately determined from a target concentration range.

Advantageously, the resistance of a cell (an object cell) having an oxygen-ion conductive member and a pair of electrodes formed on the oxygen-ion conductive member may be detected by use of the resistance detection means. For example, a constant voltage for detection of internal resistance may be applied between the electrodes of the cell, and the current flowing between the electrodes of the cell may be detected (i.e., detecting the amount of change of the current). Alternatively, a constant current for detection of internal resistance may be caused to flow between the electrodes of the cell, and the voltage between the paired electrodes of the cell may be detected (i.e., detecting the amount of change of the voltage). By use of the detected value, a CPU or the like may calculate the resistance of the cell formed from the oxygen-ion conductive member.

Other features and advantages of the invention will be set forth in, or apparent from, the detailed description of exemplary embodiments of the invention found below.

DETAIL DESCRIPTION OF EXEMPLARY EMBODIMENTS OF THE INVENTION

Figure 1:
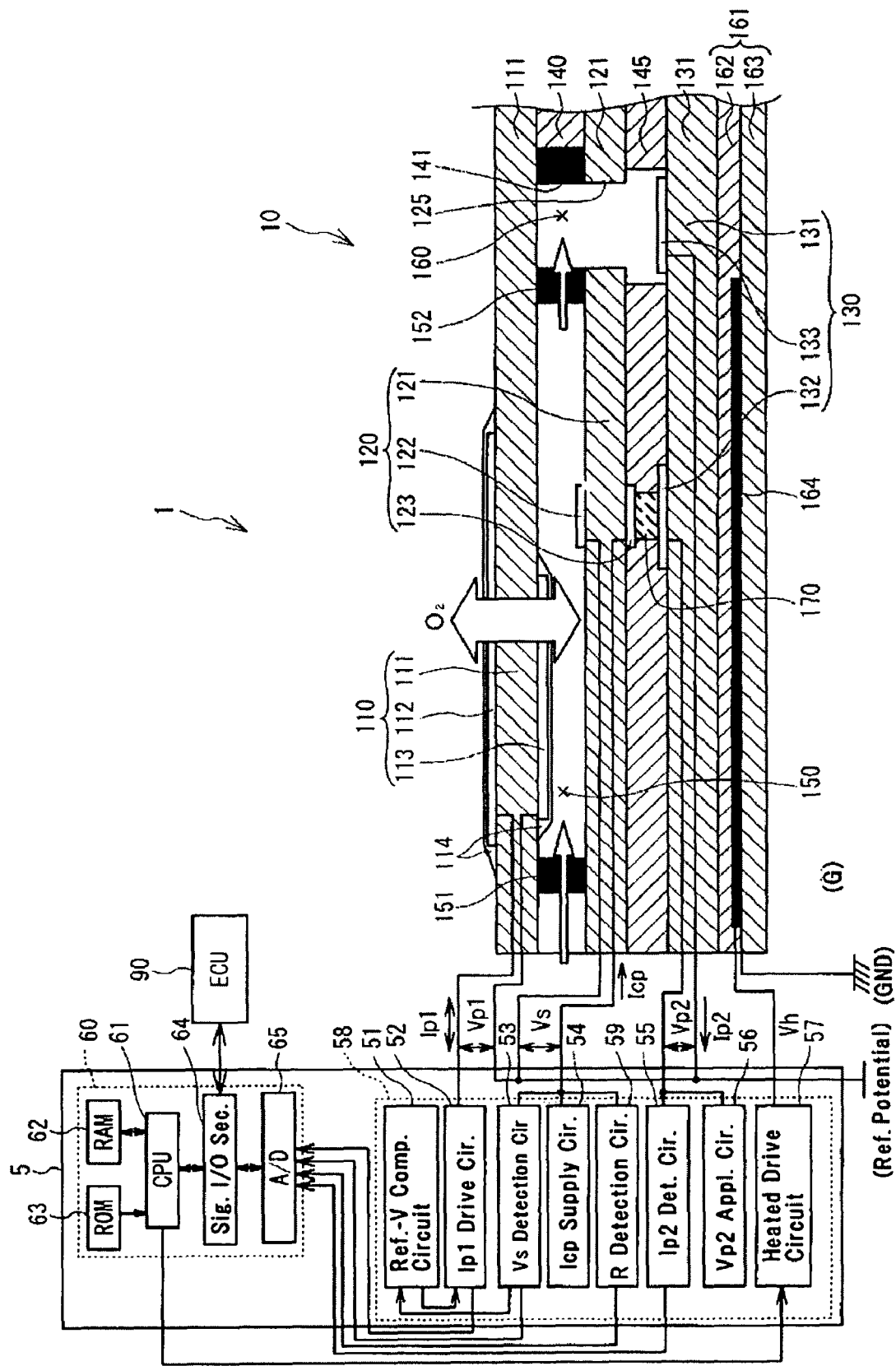
FIG. 1 is a schematic diagram of a gas sensor connected to a gas sensor control apparatus, according to an exemplary embodiment of the invention.

A gas sensor according to an embodiment of the present invention will next be described with reference to the drawings. First, referring to FIG. 1, a gas sensor 1 capable of detecting the concentration of NOx, as a specific gas will be described as an example gas sensor element according to the present invention. First, the details of the gas sensor 1 will be described. FIG. 1 shows the schematic configuration of the gas sensor 1 connected to a gas sensor control apparatus 5. FIG. 1 shows, in section, the internal structure of a front end portion of the sensor element 10 of the gas sensor 1. The left side in FIG. 1 is the front side of the sensor element 10.

In FIG. 1, the gas sensor 1 of the present embodiment has such a structure that the sensor element 10 assuming the form of a narrow elongated plate is held in a housing (not shown) used to attach the gas sensor 1 to an exhaust pipe (not shown) of an engine. Signal lines extend from the gas sensor 1 for outputting signals from the sensor element 10 and are electrically connected to the gas sensor control apparatus 5, which is mounted away from the gas sensor 1.

First, the structure of the sensor element 10 will be described. The sensor element 10 is configured such that three plate-like solid electrolyte members 111, 121, and 131 are arranged in layers with insulators 140 and 145 of alumina or the like intervening therebetween. A heater element 161 is provided on the external side (lower side in FIG. 1) of the solid electrolyte member 131. The heater element 161 includes laminated sheet-like insulating layers 162 and 163, which contain a predominant amount of alumina, and a heater pattern 164, which contains a predominant amount of Pt and is embedded between the insulating layers 162 and 163. The heater element 161, which generates heat through supply of current to the heater pattern 164, is exemplary of a "heater" as that term is used herein.

The solid electrolyte members 111, 121, and 131 are formed from a solid electrolyte of zirconia and have oxygen-ion conductivity. Porous electrodes 112 and 113 are provided on respective opposite surfaces of the solid electrolyte member 111 with respect to the direction of lamination of the sensor element 10. The electrodes 112 and 113 are formed from Pt, a Pt alloy, cermet which contains Pt and ceramic, or a like material. A porous protective layer 114 of ceramic is formed on the surface of each of the electrodes 112 and 113 for protecting the electrodes 112 and 113 from deterioration, which could otherwise result from exposure to a poisoning gas (reducing gas) contained in exhaust gas. Each of the solid electrolyte members 111, 121, and 131 is exemplary of an "oxygen-ion conductive member" as that phrase is used herein.

By causing a current to flow between the electrodes 112 and 113, the solid electrolyte member 111 can pump oxygen out and in (so-called oxygen pumping) between an atmosphere in contact with the electrode 112 (external atmosphere of the sensor element 10) and an atmosphere in contact with the electrode 113 (atmosphere in a first measurement chamber 150, which will be described later). In the present embodiment, the solid electrolyte member 111 and the electrodes 112 and 113 are collectively called an Ip1 cell 110. The Ip1 cell 110 is exemplary of a "first oxygen pump cell" as that phrase is used herein. The electrodes 112 and 113 are exemplary of "a pair of electrodes" as that phrase is used herein.

Next, the solid electrolyte member 121 is disposed in such a manner as to face the solid electrolyte member 111 with the insulator 140 intervening therebetween. Also, electrodes 122 and 123 are provided on respective opposite surfaces of the solid electrolyte member 121 with respect to the direction of lamination of the sensor element 10. Similarly, the electrodes 122 and 123 are formed from Pt, a Pt alloy, cermet which contains Pt and ceramic, or a like material. The electrode 122 is formed on a side toward the solid electrolyte member 111.

A small space serving as the first measurement chamber 150 is formed between the solid electrolyte member 111 and the solid electrolyte member 121. The electrode 113 on the solid electrolyte member 111 and the electrode 122 on the solid electrolyte member 121 are disposed in the first measurement chamber 150. When exhaust gas flowing through an exhaust path is introduced into the sensor element 10, the exhaust gas first enters the first measurement chamber 150. A porous, first diffusion resistance portion 151 is provided in the first measurement chamber 150 at a position located toward the front end of the sensor element 10; serves as a partition between the interior and the exterior of the first measurement chamber 150; and is adapted to limit inflow per unit time of exhaust gas into the first measurement chamber 150. Similarly, a second diffusion resistance portion 152 is provided in the first measurement chamber 150 at a position located toward the rear end of the sensor element 10; serves as a partition between the first measurement chamber 150 and an opening portion 141 integral with a second measurement chamber 160, which will be described later; and is adapted to limit flow per unit time of exhaust gas.

The solid electrolyte member 121 and the two electrodes 122 and 123 can cooperatively generate electromotive force according to the difference in partial pressure of oxygen between atmospheres (an atmosphere in the first measurement chamber 150 and in contact with the electrode 122 and an atmosphere in a reference-oxygen chamber 170, which will be described later, and in contact with the electrode 123) separated from each other by the solid electrolyte member 121. In the present embodiment, the solid electrolyte member 121 and the two electrodes 122 and 123 are collectively called a Vs cell 120. The Vs cell 120 is exemplary of an "oxygen-concentration detection cell" as that phrase is used herein. The electrodes 122 and 123 are exemplary of "a pair of electrodes" as that phrase is used herein.

Next, the solid electrolyte member 131 is disposed in such a manner as to face the solid electrolyte member 121 with the insulator 145 intervening therebetween. Porous electrodes 132 and 133 are provided on the solid electrolyte member 131 on a side toward the solid electrolyte member 121 and are formed from Pt, a Pt alloy, cermet which contains Pt and ceramic, or a like material. The electrodes 132 and 133 are exemplary of "a pair of electrodes" as that phrase is used herein.

The insulator 145 is absent at a position corresponding to the electrode 132 so as to form an independent small space serving as the reference-oxygen chamber 170. The electrode 123 of the Vs cell 120 is disposed in the reference-oxygen chamber 170. The reference-oxygen chamber 170 is filled with a porous body of ceramic. Also, the insulator 145 is absent at a position corresponding to the electrode 133 so as to form an independent small space serving as the second measurement chamber 160, which is separated from the reference-oxygen chamber 170 by the insulator 145. An opening portion 125 and the opening portion 141 are provided in the solid electrolyte member 121 and the insulator 140, respectively, in such a manner as to communicate with the second measurement chamber 160. As mentioned previously, the first measurement chamber 150 and the opening portion 141 are connected to each other with the second diffusion resistance portion 152 intervening therebetween.

As in the case of the above-mentioned Ip1 cell 110, the solid electrolyte member 131 and the two electrodes 132 and 133 can cooperatively pump out oxygen between atmospheres (an atmosphere in the reference-oxygen chamber 170 and in contact with the electrode 132 and an atmosphere in the second measurement chamber 160 and in contact with the electrode 133) separated from each other by the insulator 145. In the present embodiment, the solid electrolyte member 131 and the two electrodes 132 and 133 are collectively called an Ip2 cell 130. The Ip2 cell 130 is exemplary of a "second oxygen pump cell" as that phrase is used herein.

Next, the configuration of the gas sensor control apparatus 5, which is electrically connected to the sensor element 10 of the gas sensor 1, will be described. The gas sensor control apparatus 5 has a microcomputer 60, an electric circuit section 58, etc. The microcomputer 60 includes a CPU 61, RAM 62, ROM 63, a signal input/output section 64 which communicates with an ECU 90 and is connected to the electric circuit section 58 via an A/D converter 65, and an unillustrated timer clock. The electric circuit section 58 is composed of a reference-voltage comparison circuit 51, an Ip1 drive circuit 52, a Vs detection circuit 53, an Icp supply circuit 54, an Ip2 detection circuit 55, a Vp2 application circuit 56, a heater drive circuit 57, and a resistance detection circuit 59. Under control of the microcomputer 60, the electric circuit section 58 detects the $NO_x$ concentration of exhaust gas by use of the sensor element 10 of the gas sensor 1.

The electrode 113 of the Ip1 cell 110 located on the side toward the first measurement chamber 150, the electrode 122 of the Vs cell 120 located on the side toward the first measurement chamber 150, and the electrode 133 of the Ip2 cell 130 located on the side toward the second measurement chamber 160 are connected to a reference electric potential. One electrode of the heater element 161 is grounded. The Icp supply circuit 54 supplies current Icp between the electrodes 122 and 123 of the Vs cell 120 for pumping out oxygen from the first measurement chamber 150 into the reference-oxygen chamber 170. The Vs detection circuit 53 is adapted to detect voltage Vs between the electrodes 122 and 123 and outputs a detected voltage Vs to the reference-voltage comparison circuit 51. The reference-voltage comparison circuit 51 is adapted to compare the voltage Vs between the electrodes 122 and 123 of the Vs cell 120 detected by the Vs detection circuit 53 with a reference voltage (e.g., 425 mV) and outputs the result of the comparison to the Ip1 drive circuit 52.

The Ip1 drive circuit 52 is adapted to supply current Ip1 between the electrodes 112 and 113 of the Ip1 cell 110. On the basis of the result of comparison of voltage between the electrodes 122 and 123 of the Vs cell 120 with a predetermined reference voltage by the reference-voltage comparison circuit 51, the magnitude and direction of the current Ip1 are adjusted such that the voltage between the electrodes 122 and 123 of the Vs cell 120 substantially coincides with the reference voltage. As a result, the Ip1 cell 110 pumps out oxygen from the first measurement chamber 150 to the exterior of the sensor element 10 or pumps oxygen into the first measurement chamber 150 from the exterior of the sensor element 10. In other words, the Ip1 cell 110 adjusts the oxygen concentration of the first measurement chamber 150 such that the voltage between the electrodes 122 and 123 of the Vs cell 120 is maintained at a constant value (reference voltage).

The Vp2 application circuit 56 is adapted to apply voltage Vp2 (e.g., 450 mV) between the electrodes 132 and 133 of the Ip2 cell 130, and oxygen is pumped out from the second measurement chamber 160 into the reference-oxygen chamber 170. The Ip2 detection circuit 55 is adapted to detect current Ip2 flowing from the electrode 133 to the electrode 132 of the Ip2 cell 130.

The heater drive circuit 57 is controlled by the CPU 61 and is adapted to supply current to the heater pattern 164 of the heater element 161, to heat the solid electrolyte members 111, 121, and 131 (in other words, the Ip1 cell 110, the Vs cell 120, and the Ip2 cell 130), and to maintain the solid electrolyte members 111, 121, and 131 at a predetermined temperature. The heater pattern 164 is a single electrode pattern extending in the heater element 161; its one end portion is grounded; and its other end portion is connected to the heater drive circuit 57. The heater drive circuit 57 is configured to be able to perform PWM energization control on the heater pattern 164 for supplying current to the heater pattern 164 such that the solid electrolyte members 111, 121, and 131 (in the present embodiment, the solid electrolyte member 121) assume a target temperature. The heater drive circuit 57 and the CPU 61, collectively, are exemplary of a "heater control means" as that phrase is used herein.

Next, a method for measuring the internal resistance of the Vs cell 120 in the present embodiment will be described with reference to FIG. 1. The internal resistance of the Vs cell 120 is measured as follows. A constant-current source circuit provided in the resistance detection circuit 59 supplies constant current I between the electrodes 122 and 123 of the Vs cell 120. The resistance detection circuit 59 measures voltage V between the electrodes 122 and 123. By use of the measured data, the CPU 61 of the microcomputer 60 calculates the internal resistance. More specifically, a differential voltage $\Delta V$ between a voltage between the electrodes 122 and 123 as measured before the constant-current source circuit provided in the resistance detection circuit 59 supplies the constant current I to the Vs cell 120 and a voltage between the electrodes 122 and 123 as measured a predetermined period of time (e.g., 60 μs) after the constant-current source circuit supplies the constant current I to the Vs cell 120 is measured via a differential amplification circuit provided in the resistance detection circuit 59. By use of the measured data, the CPU 61 of the microcomputer 60 calculates the internal resistance. Since the configuration of the resistance detection circuit 59 and the method for measuring the internal resistance of the Vs cell 120 are known, further description is omitted. The resistance detection circuit 59 and the CPU 61, collectively, are exemplary of a "resistance detection means" as that phrase is used herein.

The present invention is not limited to measurement of the internal resistance of the Vs cell 120. The Ip1 cell 110 and the Ip2 cell 130 can also be measured for internal resistance in a manner similar to that described above.

The gas sensor control apparatus 5 having the above-described configuration detects the $NO_x$ concentration of exhaust gas by use of the sensor element 10 of the gas sensor 1. First will be described operations in detecting $NO_x$ concentration by use of the gas sensor 1.

As the heater pattern 164 rises in temperature through supply of drive current thereto from the heater drive circuit 57, the solid electrolyte members 111, 121, and 131 shown in FIG. 1 and constituting the sensor element 10 of the gas sensor 1 are heated and thus activated. By this procedure, the Ip1 cell 110, the Vs cell 120, and the Ip2 cell 130 become operable.

Exhaust gas flowing through an exhaust path (not shown) is introduced into the first measurement chamber 150 while undergoing limitation of flow as effected by the first diffusion resistance portion 151. Meanwhile, the Icp supply circuit 54 supplies a weak current Icp which flows through the Vs cell 120 from the electrode 123 to the electrode 122. Thus, oxygen contained in exhaust gas can receive electrons from the electrode 122 of negative polarity located in the first measurement chamber 150, thereby becoming oxygen ions. The oxygen ions flow through the solid electrolyte member 121 and move into the reference-oxygen chamber 170. That is, as a result of the current Icp flowing between the electrodes 122 and 123, oxygen contained in the first measurement chamber 150 is transmitted into the reference-oxygen chamber 170.

The Vs detection circuit 53 detects voltage between the electrodes 122 and 123. The reference-voltage comparison circuit 51 compares the detected voltage with a reference voltage (425 mV). The result of the comparison is output to the Ip1 drive circuit 52. By means of adjusting the oxygen concentration of the first measurement chamber 150 such that the difference in electric potential between the electrodes 122 and 123 is maintained at a constant value around 425 mV, the oxygen concentration of exhaust gas contained in the first measurement chamber 150 approaches a predetermined value ($10^{-8}$ atm to $10^{-9}$ atm).

In the case where the oxygen concentration of exhaust gas introduced into the first measurement chamber 150 is lower than the predetermined value, the Ip1 drive circuit 52 supplies the current Ip1 to the Ip1 cell 110 such that the electrode 112 assumes negative polarity, so as to pump oxygen into the first measurement chamber 150 from the exterior of the sensor element 10. By contrast, in the case where the oxygen concentration of exhaust gas introduced into the first measurement chamber 150 is higher than the predetermined value, the Ip1 drive circuit 52 supplies the current Ip1 to the Ip1 cell 110 such that the electrode 113 assumes negative polarity, so as to pump out oxygen from the first measurement chamber 150 to the exterior of the sensor element 10.

Exhaust gas whose oxygen concentration is adjusted in the first measurement chamber 150 as described above is introduced into the second measurement chamber 160 via the second diffusion resistance portion 152. In the second measurement chamber 160, $NO_x$ contained in exhaust gas comes into contact with the electrode 133 and is decomposed (reduced) into $N_2$ and $O_2$ by the catalytic effect of the electrode 133. Oxygen generated through decomposition receives electrons from the electrode 133, thereby becoming oxygen ions. The oxygen ions flow through the solid electrolyte member 131 and move into the reference-oxygen chamber 170. At this time, residual oxygen which is left unpumped out in the first measurement chamber 150 similarly moves into the reference-oxygen chamber 170 through the Ip2 cell 130. Thus, the current flowing through the Ip2 cell 130 consists of a current stemming from $NO_x$ and a current stemming from the residual oxygen. Since the residual oxygen which is left unpumped out in the first measurement chamber 150 is adjusted to a predetermined concentration as mentioned previously, the current stemming from the residual oxygen can be considered substantially constant; thus, its effect on variation in the current stemming from $NO_x$ is small. Therefore, current flowing through the Ip2 cell 130 is proportional to $NO_x$ concentration. In the gas sensor control apparatus 5, the Ip2 detection circuit 55 detects the current Ip2 flowing through the Ip2 cell 130, and, while known corrective calculation processing is performed for offset current stemming from the residual oxygen, the $NO_x$ concentration of exhaust gas is determined from the detected current.

Figure 2:
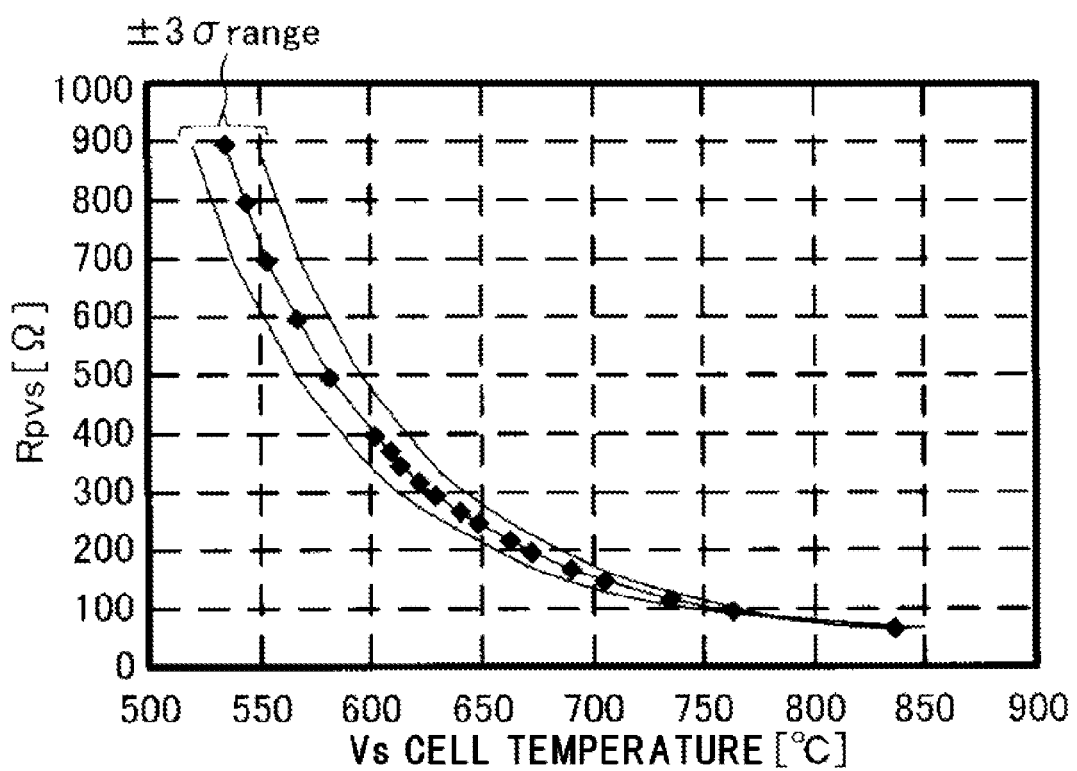
FIG. 2 is a graph showing the relation between a resistance (Rpvs) (Ω) of a Vs cell and a temperature (° C.) of the Vs cell as measured when the Vs cell is an object cell.
Figure 3:
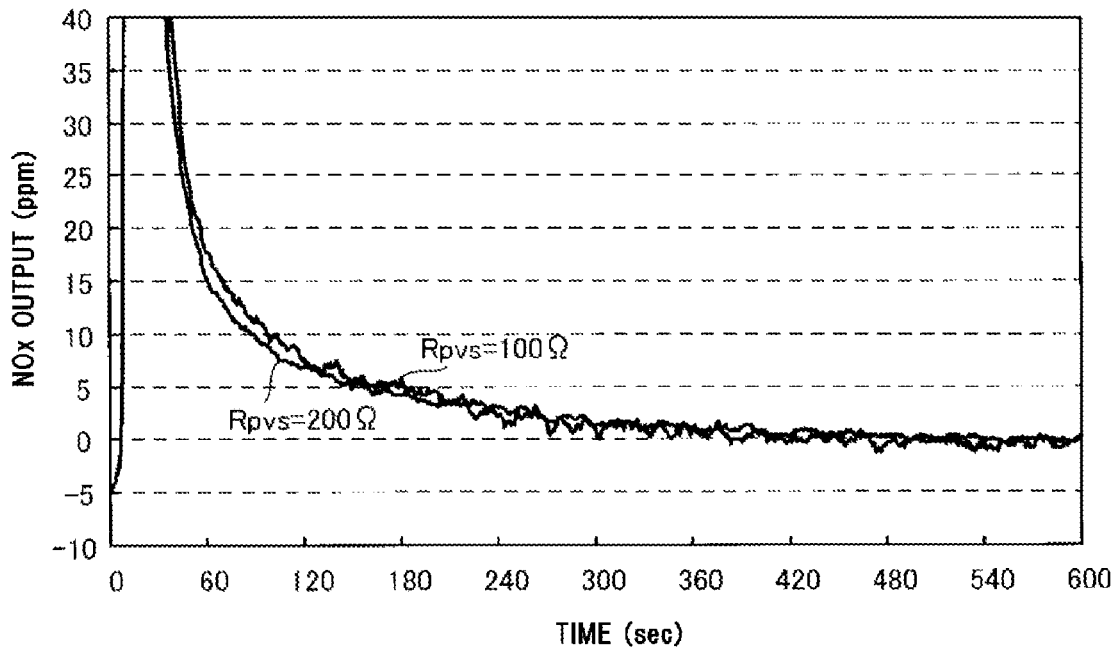
FIG. 3 is a graph showing detected $NO_x$ concentration (ppm) vs. the time that has elapsed after starting, as measured when the driving of a heater element is controlled in such a manner that the Vs cell of the gas sensor assumes a constant resistance (Rpvs) of 200Ω or 100Ω.
Figure 4:
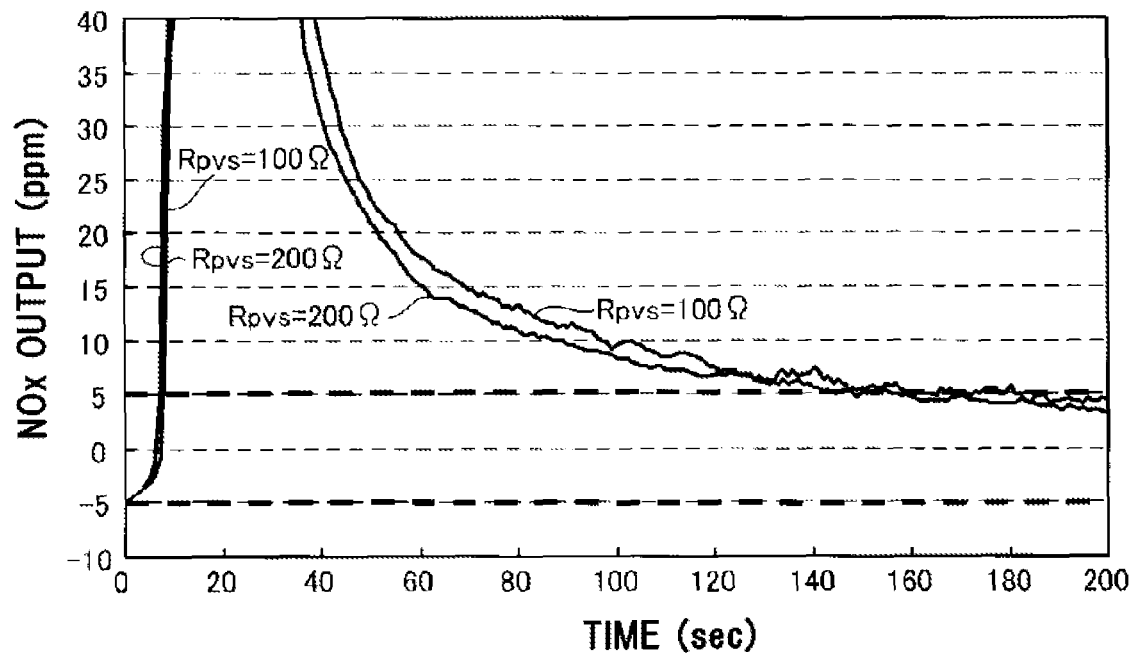
FIG. 4 is an enlarged partial view of the graph of FIG. 3.
Figure 5:
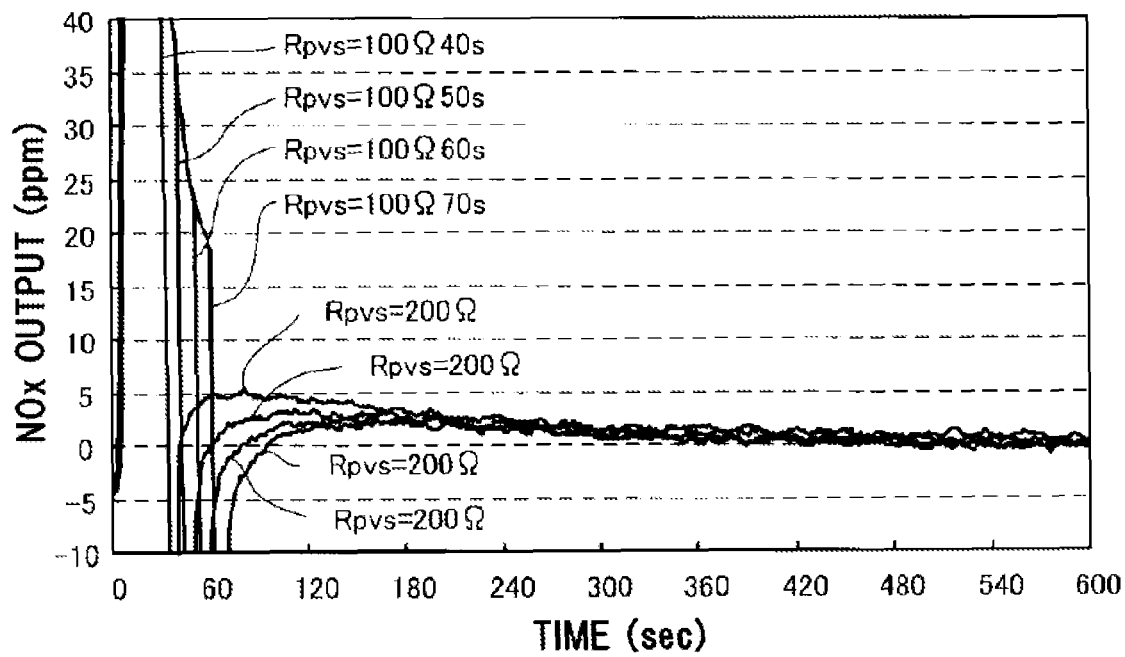
FIG. 5 is a graph showing detected $NO_x$ concentration (ppm) vs. the time that has elapsed after starting, as measured when the driving of the heater element 161 is controlled in such a manner that the Vs cell of the gas sensor assumes a constant resistance (Rpvs) of 100Ω for 40 sec, 50 sec, 60 sec, or 70 sec, and subsequently the driving of the heater element is controlled in such a manner that the Vs cell of the gas sensor assumes a constant resistance (Rpvs) of 200Ω.
Figure 6:
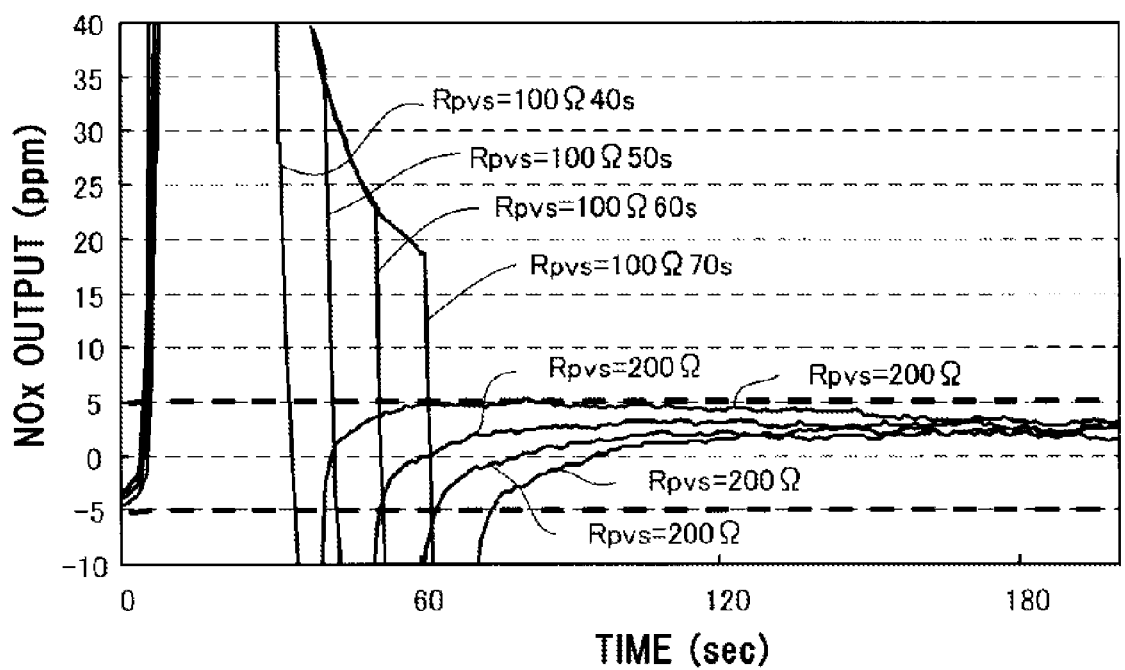
FIG. 6 is an enlarged partial view of the graph of FIG. 5.

Next, activation of the gas sensor 1 by the heater element 161 as effected by the gas sensor control apparatus 5 having the above-described configuration will be described with reference to FIGS. 2 to 6. FIG. 2 is a graph showing the relation between the resistance (Rpvs) ($\Omega$) of the Vs cell 120 and the temperature (° C.) of the Vs cell 120 as measured when the Vs cell 120 is an object cell. FIG. 3 is a graph showing detected $NO_x$ concentration (ppm) vs. the time that has elapsed after starting, as measured when the driving of the heater element 161 is controlled in such a manner that the Vs cell 120 of the gas sensor 1 assumes a constant resistance (Rpvs) of 200$\Omega$ or 100$\Omega$. FIG. 4 is an enlarged partial view of FIG. 3. FIG. 5 is a graph showing detected $NO_x$ concentration (ppm) vs. the time that has elapsed after starting as measured when the driving of the heater element 161 is controlled in such a manner that the Vs cell 120 of the gas sensor 1 assumes a constant resistance (Rpvs) of 100$\Omega$ for 40 sec, 50 sec, 60 sec, or 70 sec, and subsequently the driving of the heater element 161 is controlled in such a manner that the Vs cell 120 of the gas sensor 1 assumes a constant resistance (Rpvs) of 200$\Omega$. FIG. 6 is an enlarged partial view of FIG. 5.

First, as shown in FIG. 2, the resistance (Rpvs) of the Vs cell 120 and the temperature of the Vs cell 120 correlate with each other. When the resistance Rpvs is 900$\Omega$, the temperature of the Vs cell 120 is about 530° C.; when the resistance Rpvs is 700$\Omega$, the temperature of the Vs cell 120 is about 550° C.; when the resistance Rpvs is 400$\Omega$, the temperature of the Vs cell 120 is about 600° C.; when the resistance Rpvs is 100$\Omega$, the temperature of the Vs cell 120 is about 750° C.; and when the resistance Rpvs is 70$\Omega$, the temperature of the Vs cell 120 is about 850° C. Therefore, the temperature of the Vs cell 120 can be determined from the resistance (Rpvs) of the Vs cell 120.

Next, the activation time of the gas sensor 1 will be described with reference to FIGS. 3 to 6. When a detected $NO_x$ concentration is, for example, 0±5 ppm, the gas sensor 1 can be judged active. In other words, when the current Ip2 flowing through the Ip2 cell 130 after startup of an engine (after startup of the gas sensor control apparatus 5) stably assumes a value corresponding to a target concentration range (the detected $NO_x$ concentration: 0±5 ppm), the gas sensor 1 can be judged active. Thus, as shown in FIGS. 3 and 4, in the case where the gas sensor 1 is heated through energization of the heater element 161, and the resistance (Rpvs) of the Vs cell 120 is maintained at 100$\Omega$ or 200$\Omega$, a time of about 160 sec elapses until a detected $NO_x$ concentration, which is determined from the current Ip2 flowing through the Ip2 cell 130 and detected by the Ip2 detection circuit 55 of the gas sensor 1, converges to 0±5 ppm.

By contrast, as shown in FIGS. 5 and 6, in the case where the resistance (Rpvs) of the Vs cell 120 is first maintained at 100$\Omega$ for 40 sec, 50 sec, or 60 sec and is then maintained at 200$\Omega$, the time that elapses until a detected $NO_x$ concentration converges to 0±5 ppm is within about 60 sec. In the case where the resistance (Rpvs) of the Vs cell 120 is first maintained at 100$\Omega$ for 70 sec and is then maintained at 200$\Omega$, the time that elapses until a detected $NO_x$ concentration converges to 0±5 ppm is about 70 sec. Thus, regarding the activation time of the gas sensor 1 (the time that elapses until the current Ip2 flowing through the Ip2 cell 130 stabilizes to a value corresponding to a target $NO_x$ concentration range), the following findings have been derived. The activation time of the gas sensor 1 can be shortened through employment of a heater control mode in which energization of the heater element 161 is first controlled so as to maintain the resistance (Rpvs) of the Vs cell 120 at 100$\Omega$ for a predetermined time for imparting a high temperature to a front end portion of the Ip1 cell 110, and then energization of the heater element 161 is controlled so as to maintain the resistance (Rpvs) of the Vs cell 120 at 200$\Omega$, as compared with a heater control mode in which energization of the heater element 161 is controlled so as to maintain the resistance (Rpvs) of the Vs cell 120 at 100$\Omega$ or 200$\Omega$ (constant).

Figure 7:
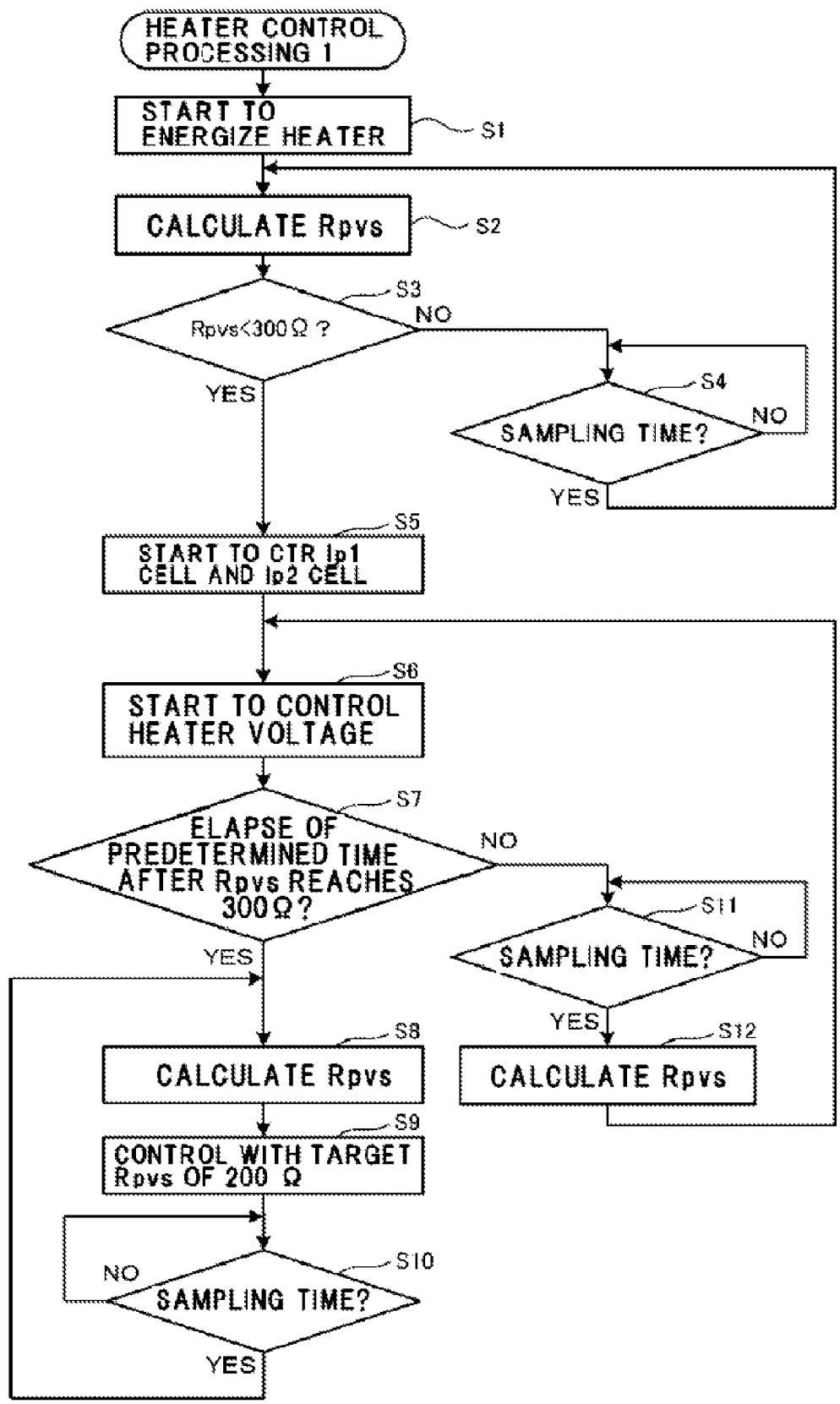
FIG. 7 is a flowchart of a method of heater control processing for controlling the heater element.
Figure 8:
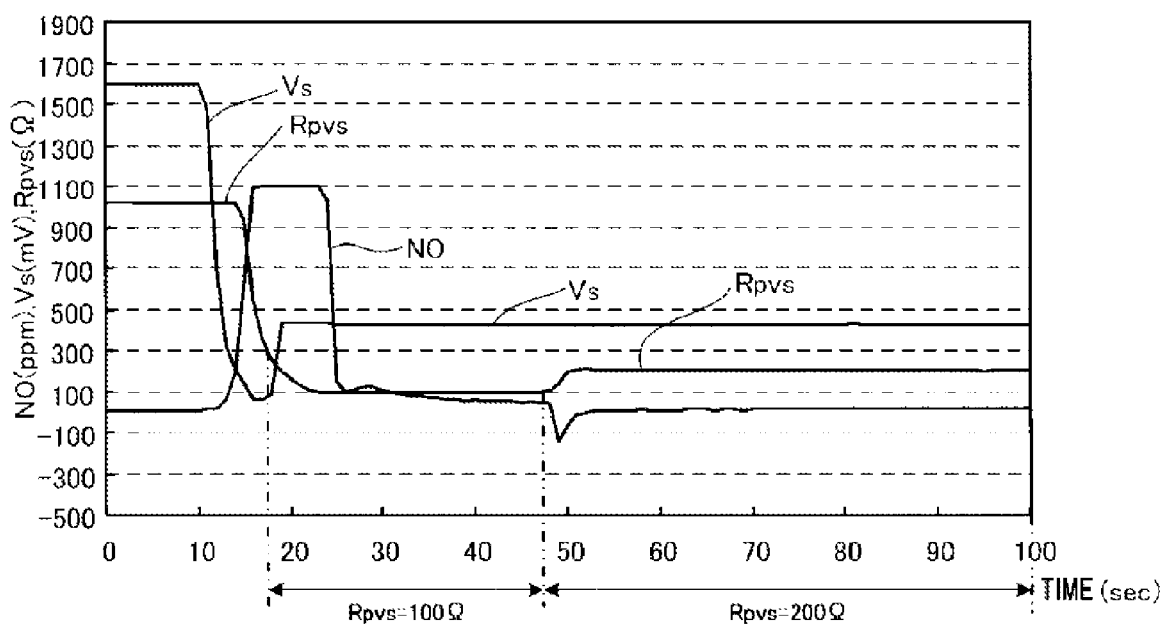
FIG. 8 is a graph showing a time-course change in a detected NO concentration (ppm), the voltage (mV) of the Vs cell, and the resistance (Rpvs) of the Vs cell.

Next, a first exemplary embodiment of a method of energization control for activation of the heater element 161 through utilization of the above-described principle will be described with reference to FIGS. 7 and 8. FIG. 7 is a flowchart of the first exemplary method ("heater control processing 1") for controlling the heater element 161. FIG. 8 is a graph showing a time-course change in a detected NO concentration (ppm), the voltage (mV) of the Vs cell 120, and the resistance (Rpvs) of the Vs cell 120. A program expressed by the flowchart shown in FIG. 7 is stored in the ROM 63 of the microcomputer 60 of the gas sensor control apparatus 5 and is executed by the CPU 61.

In the heater control processing 1, first, when sensor control start information from the ECU 90 is input to the CPU 61 via the signal input/output section 64, the CPU 61 controls the heater drive circuit 57 so as to start energization of the heater element 161 (S1). Next, the CPU 61 calculates the resistance (Rpvs) of the Vs cell 120 (S2). When the internal resistance (Rpvs) of the Vs cell 120 becomes lower than 300Ω (S3: YES), the CPU 61 starts to control the Ip1 cell 110 and the Ip2 cell 130 (S5). Next, the CPU 61 controls the heater drive circuit 57 with a target Rpvs of 100Ω so as to control energization of the heater element 161 such that the resistance (Rpvs) of the Vs cell 120 becomes 100Ω (S6). In processing of S6, measurement of time is simultaneously started. When the internal resistance (Rpvs) of the Vs cell 120 is 300Ω or higher (S3: NO), the CPU 61 stands by until the next sampling time is reached (S4: NO). When the next sampling time is reached (S4: YES), the CPU 61 returns to processing of S2. Next, when a predetermined time (e.g., 30 sec, 40 sec, 50 sec, 60 sec, or 70 sec) elapses (S7: YES) after the resistance (Rpvs) of the Vs cell 120 becomes lower than 300Ω, the CPU 61 calculates the resistance (Rpvs) of the Vs cell 120 (S8). Next, the CPU 61 controls the heater drive circuit 57 with a target Rpvs of 200Ω so as to control energization of the heater element 161 such that the resistance (Rpvs) of the Vs cell 120 becomes 200Ω (S9). Subsequently, the CPU 61 stands by until the next sampling time is reached (S10: NO). When the next sampling time is reached (S10: YES), the CPU 61 returns to processing of S8. In the case of a NO determination ("judgment") in the determination ("judgment") processing of S7 (when the predetermined time does not elapse after the resistance (Rpvs) of the Vs cell 120 becomes lower than 300Ω), the CPU 61 stands by until the next sampling time is reached (S11: NO). When the next sampling time is reached (S11: YES), the CPU 61 calculates the resistance (Rpvs) of the Vs cell 120 (S12) and subsequently returns to processing of S6. The CPU 61 which executes processing of S2, and the resistance detection circuit 59 collectively function as the "resistance detection means." The CPU 61 which executes processing of S3 functions as the "first resistance determining means." The CPU 61 which executes processing of S5 at the time of a YES determination at S3 functions as the "cell energization start means." The CPU 61 which executes processing of S9 after processing of S6, and the heater drive circuit 57 collectively function as the "heater control means." The resistance "300Ω" is an example of the "reference resistance"; the resistance "100Ω" is an example of the "first predetermined resistance"; and the resistance "200Ω" is an example of the "second predetermined resistance." According to the first embodiment, when the internal resistance (Rpvs) of the Vs cell 120 becomes an example reference resistance of 300Ω (when the temperature of the Vs cell 120 becomes a value corresponding to a resistance Rpvs of 300Ω), the Ip1 cell 110 and the Ip2 cell 130 can be energized without involvement of damage to the sensor element 10. That is, when the internal resistance (Rpvs) of the Vs cell 120 becomes 300Ω, the sensor element 10 becomes ready to measure the concentration of a specific gas. Therefore, the reference resistance is set to 300Ω.

FIG. 8 shows a time-course change in a detected NO concentration (ppm), the voltage (mV) of the Vs cell 120, and the resistance (Rpvs) of the Vs cell 120 in the case where the predetermined time for use in determination processing of S7 in the above-described heater control processing 1 is about 30 sec, and the target Rpvs for the resistance (Rpvs) of the Vs cell 120 is changed over from 100Ω to 200Ω. As is apparent from FIG. 8, when about 50 sec elapses after startup of energization of the heater element 161, an NO concentration detected by means of the Ip2 cell 130 is stabilized. Therefore, the heater control processing 1 can activate the gas sensor 1 and in turn can start measurement of $NO_x$ concentration in about 50 sec, which is greatly shorter than a conventional activation time of about 160 sec of the gas sensor 1.

Figure 9:
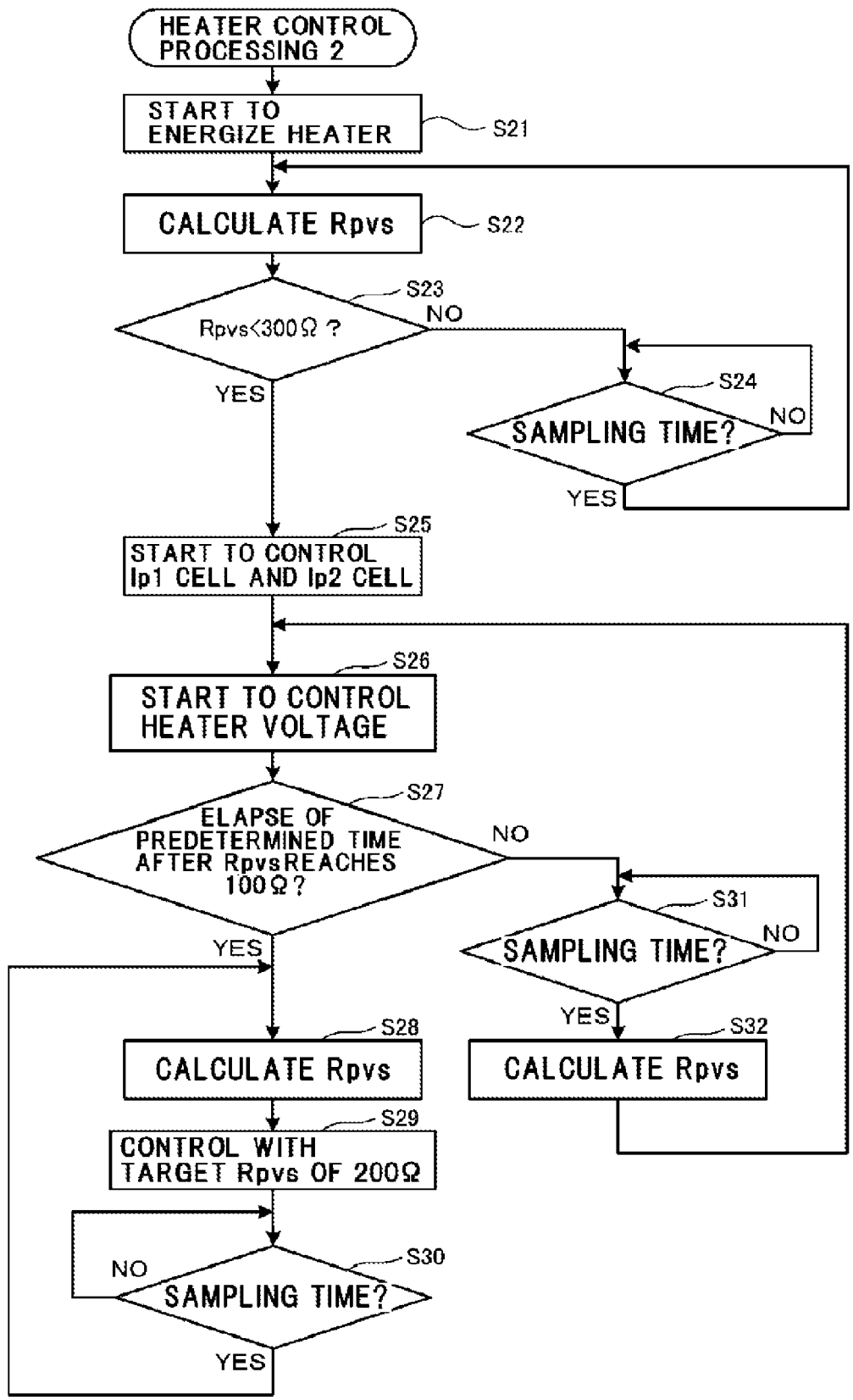
FIG. 9 is a flowchart of an alternate method of heater control processing for controlling the heater element.

Next, a second exemplary embodiment of a method of energization control for activation of the heater element 161 will be described with reference to FIG. 9. FIG. 9 is a flowchart of the second exemplary method ("heater control processing 2") for controlling the heater element 161. A program expressed by the flowchart shown in FIG. 9 is stored in the ROM 63 of the microcomputer 60 of the gas sensor control apparatus 5 and is executed by the CPU 61.

In the heater control processing 2, first, when sensor control start information from the ECU 90 is input to the CPU 61 via the signal input/output section 64, the CPU 61 controls the heater drive circuit 57 so as to start energization of the heater element 161 (S21). Next, the CPU 61 calculates the resistance (Rpvs) of the Vs cell 120 (S22). When the resistance (Rpvs) of the Vs cell 120 becomes lower than 300Ω (S23: YES), the CPU 61 starts to control the Ip1 cell 110 and the Ip2 cell 130 (S25). Next, the CPU 61 controls the heater drive circuit 57 with a target Rpvs of 100Ω so as to control energization of the heater element 161 such that the resistance (Rpvs) of the Vs cell 120 becomes 100Ω (S26). When the internal resistance (Rpvs) of the Vs cell 120 is 300Ω or higher (S23: NO), the CPU 61 stands by until the next sampling time is reached (S24: NO). When the next sampling time is reached (S24: YES), the CPU 61 returns to processing of S22. In processing of S26, measurement of time starts when the resistance (Rpvs) of the Vs cell 120 reaches 100Ω. Next, when a predetermined time (e.g., 30 sec, 40 sec, 50 sec, 60 sec, or 70 sec) elapses (S27: YES) after the resistance (Rpvs) of the Vs cell 120 reaches 100Ω, the CPU 61 calculates the resistance (Rpvs) of the Vs cell 120 (S28). Next, the CPU 61 controls the heater drive circuit 57 with a target Rpvs of 200Ω so as to control energization of the heater element 161 such that the resistance (Rpvs) of the Vs cell 120 becomes 200Ω (S29). Subsequently, the CPU 61 stands by until the next sampling time is reached (S30: NO). When the next sampling time is reached (S30: YES), the CPU 61 returns to processing of S28. In the case of a NO determination in determination processing of S27 (when the predetermined time does not elapse after the resistance (Rpvs) of the Vs cell 120 reaches 100Ω), the CPU 61 stands by until the next sampling time is reached (S31: NO). When the next sampling time is reached (S31: YES), the CPU 61 calculates the resistance (Rpvs) of the Vs cell 120 (S32) and subsequently returns to processing of S26. The CPU 61 which executes processing of S23 functions as the "first resistance determining means." The resistance "300Ω" is an example of the "reference resistance"; the resistance "100Ω" is an example of the "first predetermined resistance"; and the resistance "200Ω" is an example of the "second predetermined resistance."

As described above, even the heater control processing 2 can activate the gas sensor 1 in a time shorter than a conventional activation time of about 160 sec of the gas sensor 1.

Figure 10:
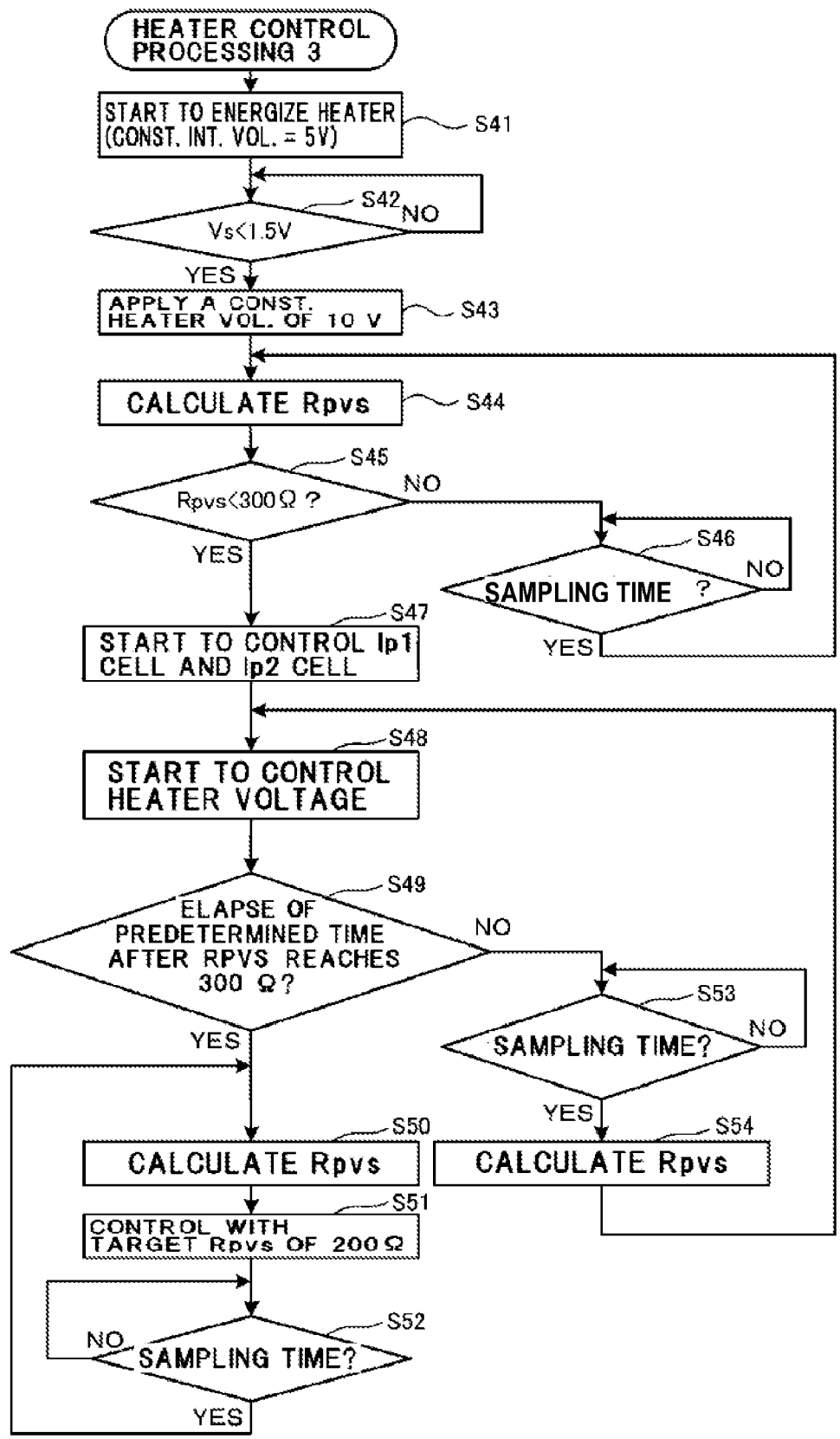
FIG. 10 is a flowchart of another alternate method of heater control processing for controlling the heater element.

Next, a third exemplary embodiment of a method of energization control for activation of the heater element 161 will be described with reference to FIG. 10. FIG. 10 is a flowchart of the third exemplary method ("heater control processing 3") for controlling the heater element 161. A program expressed by the flowchart shown in FIG. 10 is stored in the ROM 63 of the microcomputer 60 of the gas sensor control apparatus 5 and is executed by the CPU 61.

In the heater control processing 3, first, when sensor control start information from the ECU 90 is input to the CPU 61 via the signal input/output section 64, the CPU 61 controls the heater drive circuit 57 so as to start energization of the heater element 161 with an initial voltage of 5 V (S41). Next, the CPU 61 stands by until a voltage Vs of the Vs cell 120 becomes 1.5 V or lower (S42: NO). When the voltage Vs of the Vs cell 120 becomes 1.5 V or lower (S42: YES), the CPU 61 controls the heater drive circuit 57 so as to energize the heater element 161 with a voltage of 10 V (S43), and measures the resistance (Rpvs) of the Vs cell 120 (S44). Next, when the resistance (Rpvs) of the Vs cell 120 becomes lower than 300Ω (S45: YES), the CPU 61 starts to control the Ip1 cell 110 and the Ip2 cell 130 (S47). Next, the CPU 61 controls the heater drive circuit 57 with a target Rpvs of 100Ω so as to control energization of the heater element 161 such that the resistance (Rpvs) of the Vs cell 120 becomes 100Ω (S48). In processing of S45, measurement of time starts when the resistance (Rpvs) of the Vs cell 120 reaches 300Ω. When the internal resistance (Rpvs) of the Vs cell 120 is 300Ω or higher (S45: NO), the CPU 61 stands by until the next sampling time is reached (S46: NO). When the next sampling time is reached (S46: YES), the CPU 61 returns to processing of S44. Next, when a predetermined time (e.g., 30 sec, 40 sec, 50 sec, 60 sec, or 70 sec) elapses (S49: YES) after the resistance (Rpvs) of the Vs cell 120 reaches 300Ω, the CPU 61 calculates the resistance (Rpvs) of the Vs cell 120 (S50). Next, the CPU 61 controls the heater drive circuit 57 with a target Rpvs of 200Ω so as to control energization of the heater element 161 such that the resistance (Rpvs) of the Vs cell 120 becomes 200Ω (S51). The CPU 61 stands by until the next sampling time is reached (S52: NO). When the next sampling time is reached (S52: YES), the CPU 61 returns to processing of S50. In the case of a NO determination in determination processing of S49 (when the predetermined time does not elapse after the resistance (Rpvs) of the Vs cell 120 becomes lower than 300Ω), the CPU 61 stands by until the next sampling time is reached (S53: NO). When the next sampling time is reached (S53: YES), the CPU 61 calculates the resistance (Rpvs) of the Vs cell 120 (S54) and subsequently returns to processing of S48. The CPU 61 which executes processing of S42, and the Vs detection circuit 53 collectively function as the "voltage detection means." The CPU 61 which executes processing of S44 at the time of a YES determination at S42 functions as the "resistance detection means." The voltage "1.5 V" is an example of the "threshold voltage."

As described above, even the heater control processing 3 can activate the gas sensor 1 in a time greatly shorter than a conventional activation time of about 160 sec of the gas sensor 1. As in the case of S27 of the heater control processing 2 of FIG. 9, in S49, the CPU 61 may judge whether or not a predetermined time has elapsed after the resistance (Rpvs) of the Vs cell 120 reaches 100Ω.

The present invention is not limited to the above-described embodiments, but may be modified in various other forms. For example, in the embodiments, the first predetermined resistance, the second predetermined resistance, and the reference resistance are 100Ω, 200Ω, and 300Ω, respectively. However, the first predetermined resistance, the second predetermined resistance, and the reference resistance are not limited to these values, and may be freely determined so long as the relation "the first predetermined resistance<the second predetermined resistance<the reference resistance" is satisfied. In view of reliable activation of the gas sensor 1, the first predetermined resistance R1 and the second predetermined resistance R2 preferably satisfy the relation "R2−R1≧50Ω," more preferably "R2−R1≧75Ω." Notably, the inventors of the present invention have experimentally confirmed that, even when the above-described embodiments are modified such that the first predetermined resistance R1 is set to 100Ω and the second predetermined resistance R2 is set to 150Ω, the gas sensor 1 can be activated in a time shorter than a conventional gas-sensor activation time.

In the above-described embodiments, the resistance of the Vs cell 120 is measured. However, the internal resistance of the Ip1 cell 110 or the Ip2 cell 130 may be measured, and, on the basis of the measured resistance, heater control processing for controlling the heater element 161 may be executed. That is, in the case of a gas sensor having a plurality of cells, each formed from an oxygen-ion conductive member, heater control processing for controlling the heater element 161 may be executed on the basis of the internal resistance of any one of the cells.

In the above-described embodiments, the CPU 61 starts to control the Ip1 cell 110 and the Ip2 cell 130 (S5 in FIG. 7, S25 in FIG. 9, or S47 in FIG. 10) after the resistance (Rpvs) of the Vs cell 120 reaches 300Ω (S3 in FIG. 7: YES; S23 in FIG. 9: YES; or S45 in FIG. 10: YES). However, the present invention is not limited thereto. Timing for starting to control the Ip1 cell 110 and the Ip2 cell 130 may be when the temperature of the sensor element 10 reaches a predetermined value and becomes ready to be energized without involvement of damage thereto. For example, control of the Ip1 cell 110 and the Ip2 cell 130 may be started upon elapse of a predetermined time after start of heater energization. Alternatively, control of the Ip1 cell 110 and the Ip2 cell 130 may be started when the following conditions are established: as in the case of the heater control processing 3, upon determination of whether or not the voltage Vs of the Vs cell 120 is 1.5 V or lower (S42), the Vs voltage is judged to be 1.5 V or lower, and a predetermined time has elapsed after start of heater energization.

DESCRIPTION OF REFERENCE NUMERALS

1: gas sensor
5: gas sensor control apparatus
10: gas sensor element
51: reference-voltage comparison circuit
52: Ip1 drive circuit
53: Vs detection circuit
54: Icp supply circuit
55: Ip2 detection circuit
56: Vp2 application circuit
57: heater drive circuit
58: electric circuit section
59: resistance detection circuit
60: microcomputer
61: CPU
110: Ip1 cell
111: solid electrolyte member
120: Vs cell
121: solid electrolyte member
130: Ip2 cell
131: solid electrolyte member
150: first measurement chamber
161: heater element
160: second measurement chamber
170: reference-oxygen chamber

What is claimed is:

1. A gas sensor control apparatus for controlling a gas sensor including a gas sensor element comprising a plurality of cells and a heater for heating the plurality of cells, each cell of said plurality of cells comprising an oxygen-ion conductive member and a pair of electrodes formed on the oxygen-ion conductive member, wherein a current corresponding to a specific gas concentration of an object gas flows between the pair of electrodes of one cell of the plurality of cells, the gas sensor control apparatus comprising:

resistance detection means for detecting a resistance of an object cell, the object cell being any one of the plurality of cells, and heater control means for controlling energization of the heater in such a manner that the resistance detected by the resistance detection means is a first predetermined resistance corresponding to a first temperature, and subsequently further controlling energization of the heater in such a manner that the resistance detected by the resistance detection means is a second predetermined resistance corresponding to a second temperature, the second predetermined resistance of a resistance value that is higher than that of the first predetermined resistance, such that a time until an output of the gas sensor stabilizes to a value corresponding to a target gas concentration range is shortened as compared with a stabilization time of a gas sensor having a heater controlled so as to maintain a single constant resistance.

2. The gas sensor control apparatus according to claim 1, wherein the gas sensor element includes, as the plurality of cells, an oxygen-concentration detection cell for detecting an oxygen concentration of the object gas introduced into a first measurement chamber;

a first oxygen pump cell for pumping out oxygen from or pumping oxygen into the object gas contained in the first measurement chamber based on the oxygen concentration detected by the oxygen-concentration detection cell, so as to generate an adjusted gas having a controlled oxygen concentration; and a second oxygen pump cell configured such that one electrode of the pair of electrodes of the second oxygen pump cell is disposed in a second measurement chamber which communicates with the first measurement chamber and into which the adjusted gas is introduced and such that the current corresponding to the specific gas concentration of the object gas flows between the pair of electrodes of the second oxygen pump cell through application of a predetermined voltage between the pair of electrodes of the second oxygen pump cell.

3. The gas sensor control apparatus according to claim 2, further comprising voltage detection means for detecting a voltage between the pair of electrodes of the object cell, wherein, when a voltage between the pair of electrodes of the object cell becomes lower than a predetermined threshold voltage, the resistance detection means starts to measure the resistance of the object cell.

4. The gas sensor control apparatus according to claim 3, satisfying a relation $R2-R1 \geqq 50$ ohms, where $R1$ is the first predetermined resistance, and $R2$ is the second predetermined resistance.

5. The gas sensor control apparatus according to claim 2, wherein the object cell is the oxygen-concentration detection cell.

6. The gas sensor control apparatus according to claim 5, satisfying a relation $R2-R1 \geqq 50$ ohms, where $R1$ is the first predetermined resistance, and $R2$ is the second predetermined resistance.

7. The gas sensor control apparatus according to claim 2, satisfying a relation $R2-R1 \geqq 50$ ohms, where $R1$ is the first predetermined resistance, and $R2$ is the second predetermined resistance.

8. The gas sensor control apparatus according to claim 1, further comprising voltage detection means for detecting a voltage between the pair of electrodes of the object cell, wherein, when a voltage between the pair of electrodes of the object cell becomes lower than a predetermined threshold voltage, the resistance detection means starts to measure the resistance of the object cell.

9. The gas sensor control apparatus according to claim 8, satisfying a relation $R2-R1 \geqq 50$ ohms, where $R1$ is the first predetermined resistance, and $R2$ is the second predetermined resistance.

10. The gas sensor control apparatus according to claim 1, satisfying a relation $R2-R1 \geqq 50$ ohms, where $R1$ is the first predetermined resistance, and $R2$ is the second predetermined resistance.

11. A gas sensor control apparatus for controlling a gas sensor including a gas sensor element comprising a plurality of cells and a heater for heating the plurality of cells, each cell of said plurality of cells comprising an oxygen-ion conductive member and a pair of electrodes formed on the oxygen-ion conductive member, wherein a current corresponding to a specific gas concentration of an object gas flows between the pair of electrodes of one cell of the plurality of cells, the gas sensor control apparatus comprising:

resistance detection means for detecting a resistance of an object cell, the object cell being any one of the plurality of cells;

first resistance determining means for determining whether the resistance detected by the resistance detection means is lower than a predetermined reference resistance corresponding to a reference temperature;

cell energization start means for starting to energize the plurality of cells when the first resistance determining means determines that the resistance detected by the resistance detection means is lower than the predetermined reference resistance; and heater control means for, when the first resistance determining means determines that the resistance detected by the resistance detection means is lower than the predetermined reference resistance, controlling energization of the heater in such a manner that the resistance detected by the resistance detection means is a first predetermined resistance corresponding to a first temperature, the first predetermined resistance of a resistance value that is lower than that of the predetermined reference resistance, and subsequently further controlling energization of the heater in such a manner that the resistance detected by the resistance detection means is a second predetermined resistance corresponding to a second temperature, the second predetermined resistance of a resistance value that is higher than that of the first predetermined resistance and that is lower than that of the predetermined reference resistance, such that a time until an output of the gas sensor stabilizes to a value corresponding to a target gas concentration range is shortened as compared with a stabilization time of a gas sensor having a heater controlled so as to maintain a single constant resistance.

12. The gas sensor control apparatus according to claim 11, wherein the gas sensor element includes, as the plurality of cells, an oxygen-concentration detection cell for detecting an oxygen concentration of the object gas introduced into a first measurement chamber;

a first oxygen pump cell for pumping out oxygen from or pumping oxygen into the object gas contained in the first measurement chamber based on the oxygen concentration detected by the oxygen-concentration detection cell, so as to generate an adjusted gas having a controlled oxygen concentration; and a second oxygen pump cell configured such that one electrode of the pair of electrodes of the second oxygen pump cell is disposed in a second measurement chamber which communicates with the first measurement chamber and into which the adjusted gas is introduced and such that the current corresponding to the specific gas concentration of the object gas flows between the pair of electrodes of the second oxygen pump cell through application of a predetermined voltage between the pair of electrodes of the second oxygen pump cell.

13. The gas sensor control apparatus according to claim 12, further comprising voltage detection means for detecting a voltage between the pair of electrodes of the object cell, wherein, when a voltage between the pair of electrodes of the object cell becomes lower than a predetermined threshold voltage, the resistance detection means starts to measure the resistance of the object cell.

14. The gas sensor control apparatus according to claim 13, satisfying a relation R2−R1≧50 ohms, where R1 is the first predetermined resistance, and R2 is the second predetermined resistance.

15. The gas sensor control apparatus according to claim 12, wherein the object cell is the oxygen-concentration detection cell.

16. The gas sensor control apparatus according to claim 15, satisfying a relation R2−R1≧50 ohms, where R1 is the first predetermined resistance, and R2 is the second predetermined resistance.

17. The gas sensor control apparatus according to claim 12, satisfying a relation R2−R1≧50 ohms, where R1 is the first predetermined resistance, and R2 is the second predetermined resistance.

18. The gas sensor control apparatus according to claim 2, further comprising voltage detection means for detecting a voltage between the pair of electrodes of the object cell, wherein, when a voltage between the pair of electrodes of the object cell becomes lower than a predetermined threshold voltage, the resistance detection means starts to measure the resistance of the object cell.

19. The gas sensor control apparatus according to claim 18, satisfying a relation R2−R1≧50 ohms, where R1 is the first predetermined resistance, and R2 is the second predetermined resistance.

20. The gas sensor control apparatus according to claim 11, satisfying a relation R2−R1≧50 ohms, where R1 is the first predetermined resistance, and R2 is the second predetermined resistance.

* * * * *